United States Patent [19]

Seto et al.

[11] Patent Number: 5,227,403
[45] Date of Patent: Jul. 13, 1993

[54] FATS AND OILS HAVING SUPERIOR DIGESTIBILITY AND ABSORPTIVITY

[75] Inventors: Akira Seto; Osamu Yamada, both of Kanagawa, Japan

[73] Assignee: The Nisshin Oil Mills, Ltd., Tokyo, Japan

[21] Appl. No.: 780,460

[22] Filed: Oct. 23, 1991

Related U.S. Application Data

[63] Continuation of Ser. No. 488,533, Feb. 28, 1990, abandoned, which is a continuation of Ser. No. 103,142, Oct. 1, 1987, abandoned.

[30] Foreign Application Priority Data

Oct. 1, 1986 [JP] Japan .................................. 61-233423

[51] Int. Cl.$^5$ ..................... A61K 31/225; A61K 31/23
[52] U.S. Cl. ..................................... 514/547; 514/549; 554/224; 554/227
[58] Field of Search ................ 554/224, 227; 514/547, 514/549

[56] References Cited

U.S. PATENT DOCUMENTS

| | | | |
|---|---|---|---|
| 2,197,269 | 4/1940 | Guillaudeu | 260/405 |
| 3,010,925 | 11/1961 | Lynn | 260/405 |
| 3,878,231 | 4/1975 | Harwood | 260/410.7 |
| 4,172,149 | 10/1979 | Pinto et al. | 514/547 |
| 4,871,768 | 10/1989 | Bistrian et al. | 554/224 |

FOREIGN PATENT DOCUMENTS

| | | | |
|---|---|---|---|
| 620236 | 5/1961 | Canada | 260/405 |
| 0064855 | 11/1982 | European Pat. Off. | |
| 2042579 | 9/1980 | United Kingdom | |
| 8601715 | 3/1986 | World Int. Prop. O. | 514/547 |

OTHER PUBLICATIONS

Shibahashi et al., *Chemical Abstracts*, vol. 104, No. 89818; (1986).

Primary Examiner—Paul J. Killos
Assistant Examiner—B. Frazier
Attorney, Agent, or Firm—Sughrue, Mion, Zinn, MacPeak & Seas

[57] ABSTRACT

A nutrient comprising fats and oils having superior digestibility and absorptivity are provided, which fats and oils are comprised of at least one triglyceride having fatty acids of $C_8$ to $C_{14}$ at the 2-position of the triglyceride and identical unsaturated acids of $C_{18}$ or higher at both the 1- and 3-positions thereof. Examples of the unsaturated fatty acids of $C_{18}$ or higher are linolic acid, linolenic acid, arachidonic acid, eicosapentaenoic acid, and docosahexaenoic acid.

7 Claims, No Drawings

FATS AND OILS HAVING SUPERIOR DIGESTIBILITY AND ABSORPTIVITY

This is a continuation of application Ser. No. 07/488,533 filed Feb. 29, 1990, now abandoned, which is a continuation of application Ser. No. 07/103,142 filed Oct. 1, 1987, now abandoned.

BACKGROUND OF THE INVENTION

1. Field of the Invention

This invention relates to fats and oils having superior digestibility and adsorptivity, and more particularly it relates to fats and oils consisting of triglycerides having a short chain fatty acid of $C_{14}$ or less at the 2-position thereof.

2. Description of the Related Art

Natural fats and oils include plant fats and oils represented by soybean oil, rape seed oil, safflower seed oil, etc. and animal fats and oils such as beef tallow, fish oils, etc. and they have specific features that the former contains a large quantity of linolic acid as an essential fatty acid, while the latter contains short chain and $C_{20}$ or higher highly unsaturated fatty acids such as eicosapentaenoic acid (EPA), docosahexaenoic acid (DHA), etc. In particular, in view of the fact that linolic acid exhibits an effectiveness of reducing serum cholesterol, while EPA and DHA have a function of inhibiting thrombocyte agglutination as well as a function of reducing serum cholesterol and exhibit an effectiveness of preventing brain thrombus, it has been urged that intake of these long chain highly unsaturated fatty acids is important for health maintenance. Thus, use of safflower oil and purified products of fish oils for various foods has been being increasing, but the digestibility and absorptivity of fats and oils containing a large quantity of these fatty acids cannot be said to be so good. In particular, the problem of the digestibility and absorptivity has been becoming more serious for persons emaciated in the digestion function as in patients and old persons.

On the other hand, it has been known that unlike such long chain fatty acids, fats and oils composed only of shorter chain fatty acids of 8 to 12 carbon atoms, i.e., medium chain fatty acid triglycerides, are very rapid in the absorption and also easy in the metabolism; hence they have been used as the lipid source of fluid foods, etc. However, such medium chain fatty acid triglycerides have often caused side effects such as acosmia of alimentary canals such as diarrhea accompanying the rapid absorption and metabolism, formation of ketone substances at the time of intake of a large quantity thereof, etc.

Thus, since it is difficult to use a large quantity of medium chain triglycerides as an energy source, it has been recommended to supplement use medium fatty acid triglycerides with long chain fatty acid triglycerides. As a process for such simultaneous use, a process of merely nixing the both, and a process of mixing the both followed by random ester exchange therebetween, have been proposed. However, these processes are still insufficient in the aspect of digestibility and absorptivity.

SUMMARY OF THE INVENTION

The object of the present invention is to provide a nutrient comprising fats and oils which overcome drawbacks as seen in conventional products and having improved effectiveness thereof, and having superior digestibility and absorptivity.

The present invention is directed to a nutrient comprising triglyceride(s) having superior digestibility and absorptivity, comprising at least one triglyceride having a fatty acid of $C_8$ to $C_{14}$ at the 2-position of the triglyceride and identical unsaturated fatty acids of $C_{18}$ or higher at both the 1- and 3-positions thereof, said at least one triglyceride having identical unsaturated acids at both the 1- and 3-positions thereof being present in said nutrient in a proportion sufficient to improve digestibility and reduce acosmia.

DETAILED DESCRIPTION OF PREFERRED EMBODIMENTS

Concerning the triglyceride(s) of this invention, as the fatty acid at the 2-position, those of $C_8$ to $C_{14}$ are required and those of $C_8$ to $C_{12}$ are preferred. The degree of unsaturation of these fatty acids has no particular limitation, but saturated or monounsaturated acids are preferred in the aspect of stability, etc.

The identical unsaturated fatty acids at both the 1- and 3-positions have no particular limitation as they are of long chain type of $C_{18}$ or higher and have one or more carbon-carbon double bonds, and various kinds thereof may be used depending on the desired properties and physiological effect of the fats and oils. The upper limit of carbon atoms of the above fatty acid is preferably 24. For example, linolic acid and linolenic acid as essential fatty acids, EPA and DHA having been noted to exhibit effects of preventing brain thrombus, arachidonic acid as a precursor of prostaglandin having various physiological functions, etc. may be used.

The present invention is characterized by the fact that the nutrients include at least one kind of triglycerides of which the 2-position is a fatty acid of $C_8$ to $C_{14}$ and both the 1- and 3-positions are identical unsaturated fatty acids of $C_{18}$ or higher.

The fats and oils of the present invention wherein linolic acid or linolenic acid is used as the fatty acids at both the 1- and 3-positions in the triglycerides are higher in the absorption rate of linolic acid or linolenic acid than the case of intake of safflower oil or soybean oil (most of the fatty acids of these triglycerides being long chain unsaturated fatty acids of $C_{18}$ or more and having few specificity at the sites linked to glycerol).

Further, since arachidonic acid, EPA and DHA each have a large molecular chain-length diameter, they are further inferior in the digestion and absorption rates to fatty acids of $C_{18}$ so that even if fish oils, etc. containing a large quantity thereof are administered as they are, effectiveness is difficultly exhibited, whereas according to the fats and oils of the present invention, it is possible to achieve a higher effectiveness even in the same dose.

In the production of the fats and oils of the present invention, since the position specificity of the 1- and 3-positions and 2-position is required, it is preferred to employ an ester exchange process by means of a ligase having a specifity at both the 1- and 3-positions of glyceride. Namely, to one mol of a triglyceride composed only of short chain fatty acids such as synthesized medium chain fatty acid triglycerides, cocoa butter, palm fat, etc. are added 2 to 3 mols of unsaturated fatty acids such as linolic acid, EPA, etc. or unsaturated fatty acid esters or nearly the same mols of triglycerides, followed by carrying out ester exchange with a lipase having at both 1-and 3-positions specificity. After completion of the ester exchange, free fatty acids, fatty acid esters, glycerine, triglycerides, etc. are removed according to a conventional method such as alkali washing, steam distillation, molecular distillation, treatment with high molecular membranes, treatment with ion exchange resins, column chromatography, etc. to thereby obtain the aimed fats and oils.

As the lipase having a specificity at both the 1- and 3-positions, commercially available products such as LIPOZYME (tradename of a product manufactured by NOVO Company), TALIPASE (tradename of a product manufactured by Tanabe Seiyaku Company), lipase (mafufactured by Seikagaku Kogyo Company), Lipase D, Lipase F-AP, Lipase M-AP, Lipase AP and Lipase R (tradenames of products manufactured by Amano Seiyaku Company, respectively), etc. may be used.

In addition, the fats and oils may also be produced according to synthetic methods.

The fats and oils contained in the nutrient of the present invention obtained by the above-mentioned method comprises at least one triglyceride having a fatty acid of $C_8$ to $C_{14}$ at the 2-position of the triglyceride and identical unsaturated fatty acids of $C_{18}$ or higher at both the 1- and 3-positions thereof.

Since the fats and oils of the present invention are usually in the form of liquid at room temperature, it is possible to use them in various forms. For example, in the case of foods, they may be used for dressing, mayonnaise, etc. or as a fat or oil component of fluid foods for remedy. Further, as pharmaceuticals, when they are used as a fat or oil component of oral or intravascular nutrients, a substrate for suppository, a fat or oil component of transfusion (fatty emulsion for intravenous injection), etc., it is possible to produce a product having a superior absorption effectiveness to those of conventional LCT or simultaneous use of LCT with MCT.

Further, the fats and oils of the present invention may also be used as those to be added to feedstuffs for fisheries or stock-raising. Namely, mammals and fishes are generally weak in the digestibility and absorptivity at their infant period so that unless fats and oils are adequately fed, obstacles such as diarrhea may often occur. Thus, even in such a case, use of the fats and oils of the present invention is effective.

The fats and oils contained in the nutrient of the present invention which comprises at least one triglyceride having identical unsaturated fatty acids at both the 1- and 3-positions of the triglyceride are present in the above-mentioned nutrient in a proportion sufficient to improve digestibility and reduce acosimia.

In addition, in various use applications, it is not always necessary to singly use the fats and oils of the present invention. It is optional to blend other fats and oils with those of the present invention to such an extent that the effectiveness of the present invention is not harmed, and use the resulting blend.

The present invention will be described in more detail by way of Examples.

EXAMPLE 1

Six mols of safflower oil fatty acid (the content of linolic acid in the total fatty acid: 70%) were added to an equimolecular mixture of capric acid ($C_8$) with caprylic acid ($C_{10}$), followed by subjecting the resulting mixture to the following two kinds of ester exchange reactions: (1) Ten parts of a lipase having a specificity at the 1- and 3-positions (LIPOZYME, tradename of a product manufactured by NOVO Company) were added to 100 parts of the above-mentioned mixture, followed by carrying out reaction with weak stirring at 60° C. for 5 hours. (2) Ten parts of a lipase having no specificity at the 1- and 3-positions (Lipase OF, tradename of a product manufactured by Meito Sangyo Company) were added to 100 parts of the above-mentioned mixture, followed by carrying out reaction at 40° C. for 5 hours.

After completion of the reaction, the enzymes were filtered off, followed by washing the resulting material with an alkaline aqueous solution in a conventional manner to remove free fatty acids, further washing with purified water, dehydrating with sodium sulfate to obtain two kinds of ester exchange fats and oils (a product by way of the reaction (1) being referred to as SE and a product by way of the reaction (2) being referred to as RE).

The respective fatty acid compositions of SE and RE are shown in Table 1.

TABLE 1

| | Fatty acid distribution of SE and RE | | | | | |
|---|---|---|---|---|---|---|
| | Total fatty acids | | Fatty acids at 1- and 3-positions | | Fatty acids at 2-position | |
| | SE | RE | SE | RE | SE | RE |
| $C_{8:0}$*) | 16.2 | 15.0 | 7.9 | 15.7 | 47.2 | 14.7 |
| $C_{10:0}$ | 14.8 | 12.1 | 5.1 | 12.2 | 44.8 | 11.5 |
| $C_{14:0}$ | — | — | — | — | — | — |
| $C_{16:0}$ | 3.6 | 4.5 | 5.4 | 4.9 | 0.4 | 4.2 |
| $C_{16:1}$ | — | — | — | — | — | — |
| $C_{18:0}$ | 2.8 | 3.4 | 3.0 | 3.2 | 0.3 | 4.0 |
| $C_{18:1}$ | 5.2 | 8.1 | 11.0 | 7.6 | 0.7 | 7.0 |
| $C_{18:2}$ | 55.1 | 56.1 | 67.0 | 56.0 | 6.0 | 57.0 |
| $C_{18:3}$ | — | — | — | — | — | — |
| Others | 2.3 | 0.8 | 0.6 | 0.4 | 0.6 | 1.0 |

*)The numeral figure on the left side represents the number of carbon atom and that on the right side represents the number of double bond.

Next, 5 kinds of fats and oils of SE, RE, MCT, safflower oil and a mixture of MCT/safflower oil (1:2) were each subjected to a digestibility and absorptivity test with rats. As the rats, those of SD genus (body weight 100 g, male) were used. Rats of test sections were fed with a non-fatty food for 3 days, followed by further feeding them with feedstuffs obtained by adding the above-mentioned respective fats and oils each in 15% by weight to the above non-fatty food for 3 days and collecting the respective total feces during 6 days.

On the other hand, rats of control sections were fed with the non-fatty food for 6 days, followed by similarly collecting the respective total feces.

In addition, 10 rats were used in each of the respective test sections and the control sections.

The compositions of the above-mentioned non-fatty food and the above food having the fats and oils added are shown in Table 2.

TABLE 2

| | Compositions of feedstuffs | |
|---|---|---|
| | Non-fatty food | Fats and oils-added food |
| Casein | 220 | 220 |
| Glucose | 738 | 588 |
| Fats and oils | 0 | 150 |
| Salt mixture | 40 | 40 |
| Vitamine mixture | 1 | 1 |
| Choline chloride | 1 | 1 |

The collected total feces was freeze-dried and subjected to lipid extraction with a mixed solvent of hexane/ethanol (2:1). The respective total quantities of fatty acids in the total feces were measured according to gas chromatography. The numeral values obtained by subtracting those of the control sections from those of the test sections were presumed to be the quantities absorbed and rendered as the percentages of digestion and absorption of the respective fats and oils. The results are shown in Table 3.

TABLE 3

| | Digestivities and absorptivities of various triglycerides | |
|---|---|---|
| | Percentage absorption of fats and oils taken (%) | Presence or absence of diarrhea* |
| SE | 93.8 ± 0.52 | — |
| RE | 74.3 ± 0.40 | — |
| MCT | 70.3 ± 1.20 | ++ |
| Safflower oil | 78.6 ± 1.58 | + |
| MCT/safflower oil | 80.4 ± 0.46 | + |

* —: no abnormality, +: slight diarrhea, ++: notable diarrhea (this applies to the succeeding).

EXAMPLE 2

Ester exchange reaction was carried out in the same manner as in (1) and (2) of Example 1 expect that as the fats and oils used at the time of ester exchange of Example 1, MCT was changed to trimyristin and safflower oil fatty acids were changed to EPA (eicosapentaenoic acid) having a purity of 95%, followed purification to obtain two kinds of ester exchange reaction fats and oils (those obtained according to the above reaction (1) being referred to as SE-2 and those according to the reaction (2) being referred to as RE-2). However, in the case of use of EPA, the temperature was made 35° C. and the reaction time was made 12 hours.

Further, with 5 kinds of fats and oils of SE-2, RE-2, trimyristin, EPA triglyceride (purity:95%) and a mixture of trimyristin/EPA triglyceride (1:2), digestion and absorption tests were carried out in the same manner as in Example 1. The results are shown in Table 4.

TABLE 4

| | Digestibility and absorptivity of various triglycerides | |
|---|---|---|
| | Percentage absorption of fats and oils taken (%) | Presence or absence of diarrhea |
| SE-2 | 92.8 ± 0.96 | — |
| RE-2 | 68.1 ± 1.80 | — |
| Trimyristin | 65.3 ± 1.90 | — |
| EPA triglyceride | 70.1 ± 0.89 | + |
| Trimyristin/EPA | 67.2 ± 1.60 | + |

EXAMPLE 3

With the fats and oils (SE and SE-2) prepared in Examples 1 and 2, performance comparisons thereof with mother's milk lipid and lard, both having been said to have a very good digestibility and absorptivity were carried out. The measurement method of digestibility and absorptivity are the same as in Example 1. The results are shown in Table 5.

TABLE 5

| | Digestibilities and absorptivities of various kinds of triglycerides | |
|---|---|---|
| | Percentage absorption of fats and oils taken (%) | Presence or absence of diarrhea |
| SE | 93.8 ± 0.52 | — |
| SE-2 | 92.8 ± 0.96 | — |
| Mother's milk lipid | 90.3 ± 0.56 | — |
| Lard | 88.6 ± 0.48 | — |

EXAMPLE 4

With (1) a lipase having a specifity at the 1- and 3-positions (Talipase, tradename of a product manufactured by Amano Seiyaku Company) or (2) a lipase having no specifity at the 1- and 3-positions (Lipase P, tradename of a product manufactured by Amano Seiyaku Company), 3 mols of linolic acid (a reagent manufactured by Wako Junyaku Company, purity 95%) were reacted with one mol of a medium chain fatty acid triglyceride (composition ratio of MCT: fatty acid, $C_8/C_{10}=75/25$) to subject these in the same manner as in Example 1 to ester exchange reaction, followed by removing the lipases and free fatty acids in a conventional manner, to obtain two kinds of ester exchange fats and oils according to a combination of solvent-fractionation process with column chromatography process (product by means of (1) being referred to as SE-3 and that by means of (2) being referred to as RE-3). The fatty acid compositions of SE-3 and RE-3 are shown in Table 6.

TABLE 6

| Fatty acid distribution of SE-3 and RE-3 | | | | | | |
|---|---|---|---|---|---|---|
| | Total fatty acids | | Fatty acids at 1- and 3-positions | | Fatty acid at 2-position | |
| | SE-3 | RE-3 | SE-3 | RE-3 | SE-3 | RE-3 |
| $C_{8:0}$ | 26.5 | 24.5 | 5.0 | 23.0 | 72.6 | 20.2 |
| $C_{10:0}$ | 9.9 | 8.0 | 2.6 | 17.7 | 21.0 | 18.1 |
| $C_{14:0}$ | — | — | — | — | — | — |
| $C_{16:0}$ | — | — | — | — | — | — |
| $C_{16:1}$ | — | — | — | — | — | — |
| $C_{18:0}$ | — | — | — | — | — | — |
| $C_{18:1}$ | 3.0 | 2.4 | 1.5 | 0.6 | 0.1 | 0.8 |
| $C_{18:2}$ | 63.0 | 64.3 | 90.4 | 58.5 | 5.8 | 60.5 |
| $C_{18:3}$ | — | — | — | — | — | — |
| Others | 1.0 | 0.8 | 0.5 | 0.2 | 0.5 | 0.4 |

Next, with 3 kinds of fats and oils of SE, SE-3 and RE-3, digestibility and absorptivity tests were carried out in the same manner as in Example 1. The results are shown in Table 7.

TABLE 7

| | Digestibility and absorptivity of various triglycerides | |
|---|---|---|
| | Percentage absorption of fats and oils taken (%) | Presence or absence of diarrhea |
| SE | 93.8 ± 0.52 | — |
| SE-3 | 98.1 ± 0.29 | — |
| RE-3 | 73.0 ± 0.51 | — |

The fats and oils of the present invention have a far higher digestibility and absorptivity than safflower oil, fish oils, etc. Thus, the fats and oils of the present invention have a higher efficiency of absorption of linolic acid, EPA, etc. than safflower oil, fish oils, etc.; hence they are very useful.

Further, there is no fear of diarrhea and side effects as observed in the case of MCT.

What we claim is:

1. A nutrient comprising triglyceride(s) comprising at least one triglyceride having a fatty acid of $C_8$ to $C_{14}$ at the 2-position of the triglyceride and identical unsaturated fatty acids of $C_{18}$ or higher at both the 1- and 3-positions thereof, said at least one triglyceride having identical unsaturated fatty acids at both the 1- and 3-positions thereof being present in said nutrient in a proportion sufficient to improve digestibility and reduce acosmia.

2. A nutrient according to claim 1 wherein said fatty acid at the 2-position of said triglyceride is a fatty acid of $C_8$ to $C_{12}$.

3. A nutrient according to claim 1 wherein the unsaturated fatty acid at both the 1- and 3-positions of said triglyceride is a fatty acid selected from the group consisting of linolic acid and linolenic acid.

4. A nutrient according to claim 1 wherein said unsaturated fatty acid at both the 1- and 3-positions of said triglyceride is a fatty acid selected from the group consisting of arachidonic acid, eicosapentaenoic acid and docosahexaenoic acid.

5. A nutrient according to claim 1, in a pharmacologically acceptable form for use as an oral or intravascular nutrient.

6. A nutrient according to claim 1, in the form of a pharmacologically acceptable emulsion for use for intravenous injection.

7. The nutrient according to claim 1, produced by subjecting a triglyceride having a fatty acid chain of $C_8$ to $C_{14}$ at the 2-position to an ester exchange reaction in the presence of an unsaturated fatty acid having 18 or more carbon atoms, its alcohol ester, triglyceride, or salt and a lipase giving a specificity at both the 1- and 3-positions.

* * * * *